United States Patent [19]

Francis et al.

[11] Patent Number: 5,059,002
[45] Date of Patent: Oct. 22, 1991

[54] SECOND HARMONIC GENERATION WITH ACHIRAL, STRAIGHT-CHAIN CARBAMIC ACID DERIVATIVES

[75] Inventors: Cecil V. Francis; George V. D. Tiers, both of St. Paul, Minn.

[73] Assignee: Minnesota Mining and Manufacturing Company, St. Paul, Minn.

[21] Appl. No.: 454,755

[22] Filed: Dec. 21, 1989

[51] Int. Cl.$^5$ .............................................. G02F 1/01
[52] U.S. Cl. .................................... 359/328; 359/241
[58] Field of Search ...................... 350/354, 96.34, 353; 307/425, 427; 252/582, 600; 372/22

[56] References Cited

U.S. PATENT DOCUMENTS

| | | | |
|---|---|---|---|
| 3,034,700 | 5/1962 | Hickman | 230/101 |
| 3,395,329 | 7/1968 | Rentzepis | 321/69 |
| 3,431,484 | 3/1969 | Pao et al. | 321/69 |
| 3,858,124 | 12/1974 | Bass et al. | 332/7.51 |
| 4,199,698 | 4/1980 | Bethea et al. | 307/425 |
| 4,431,263 | 2/1984 | Garito | 350/96.34 |
| 4,756,598 | 7/1988 | Gerbi et al. | 350/96.29 |
| 4,807,968 | 2/1989 | Leslie | 350/311 |
| 4,808,332 | 2/1989 | DeMartino et al. | 526/312 |
| 4,810,338 | 3/1989 | DeMartino et al. | |
| 4,818,616 | 4/1989 | Milverton et al. | 428/411.1 |
| 4,818,802 | 4/1989 | Choe | 526/305 |
| 4,818,898 | 4/1989 | Anderson et al. | 307/427 |
| 4,818,899 | 4/1989 | Tiers | 307/425 |
| 4,822,865 | 4/1989 | DeMartino et al. | 526/292.2 |
| 4,824,219 | 4/1989 | Choe | 350/354 |
| 4,826,950 | 5/1989 | DeMartino | 528/292 |
| 4,828,758 | 5/1989 | Gillberg-LaForce et al. | 252/582 |
| 4,835,235 | 5/1989 | DeMartino et al. | 526/311 |
| 4,851,270 | 7/1989 | Che et al. | 428/1 |
| 4,855,078 | 8/1989 | Leslie | 252/582 |
| 4,855,376 | 8/1989 | DeMartino et al. | 526/311 |
| 4,861,129 | 8/1989 | Che et al. | 350/96.13 |
| 4,865,430 | 9/1989 | DeMartino et al. | 350/376 |
| 4,867,538 | 9/1989 | Yoon et al. | 350/350 R |
| 4,867,540 | 9/1989 | DeMartino | 350/355 |
| 4,868,250 | 9/1989 | DeMartino et al. | 525/479 |

FOREIGN PATENT DOCUMENTS 0257888 3/1988 European Pat. Off. .
0271251 6/1988 European Pat. Off. .

OTHER PUBLICATIONS

Bunn, C. W., *Chemical Crystallography*, Second Edition, Clarendon Press, Oxford, England, 1961, pp. 321-322.
"Use of the Pyroelectric Effect to Determine the Absolute Orientation of the Polar Axis in Molecular Crystals", Patil, A. A., Curtin, D. Y., and Paul, I. C., J. Am. Chem. Soc., 1985, 107, 726-727.
Kurtz and Perry, J. Appl. Phys., 39, 3798-3812 (1968).

Primary Examiner—William Mintel
Assistant Examiner—Roy Potter
Attorney, Agent, or Firm—Gary L. Griswold; Walter N. Kirn; David L. Weinstein

[57] ABSTRACT

Devices for and method of generating coherent second harmonic light radiation. The devices comprise a laser source of coherent light radiation at a fixed fundamental frequency, an acentrically crystalline, achiral, straight-chain N-nitrophenyl carbamyl compound, means for directing the output radiation of the laser onto the acentrically crystalline, achiral, straight-chain N-nitrophenyl carbamyl compound, and output means for utilizing the second harmonic frequency. N-nitrophenyl carbamyl compounds, and acentric crystals thereof that are capable of being used in the aforementioned devices and method, are also described herein.

8 Claims, 1 Drawing Sheet

Fig. 1

SECOND HARMONIC GENERATION WITH ACHIRAL, STRAIGHT-CHAIN CARBAMIC ACID DERIVATIVES

BACKGROUND OF THE INVENTION

1. Technical Field

This invention is concerned with materials for nonlinear optical devices for conversion of optical energy at one frequency to optical energy at another frequency.

2. Discussion of the Prior Art

Laser techniques have been developed that make it convenient to obtain various fundamental frequencies of coherent laser light by utilizing solid, gas, and liquid media. Outstanding among these are solid-state lasers, because they are small, inexpensive, and require no maintenance; their output is limited to the near-infrared region of the spectrum and is of low power. However, in many applications, laser light having frequencies not among those conveniently obtainable is required. Nonlinear optical crystals have, therefore, frequently been employed to convert coherent laser light of a fundamental frequency into coherent light of its second harmonic, that is to say, coherent light with a frequency twice the fundamental frequency. This conversion is termed "second harmonic generation" (SHG).

Use of organic molecules in nonlinear optical devices has generated much interest recently because many molecules are available for investigation. Some substituted aromatic molecules are known to exhibit large optical nonlinearities. The possibility of such an aromatic molecule having large optical nonlinearities is enhanced if the molecule has electron donor and acceptor groups bonded at opposite ends of the conjugated electronic system of the molecule. Potential utility for very high frequency application of organic materials having large second-order and third-order nonlinearities is greater than that for conventional inorganic electro-optic materials because of the bandwidth limitations of inorganic materials. Furthermore, properties of organic materials can be varied to optimize mechanical and thermo-oxidative stability and laser damage threshold.

U.S. Pat. No. 4,199,698 discloses that the nonlinear optical properties of one crystal form of 2-methyl-4-nitroaniline (MNA) make it a highly useful material in nonlinear devices that convert coherent optical radiation including a first frequency into coherent optical radiation including a second, typically doubled, frequency. Nonlinear devices have means for introducing coherent radiation of a first frequency into the MNA and means for utilizing coherent radiation emitted from the MNA at a second frequency. U.S. Pat. No. 4,431,263 discloses that diacetylenes and polymers formed from diacetylenic species, which are amenable to close geometric, steric, structural, and electronic control, provide nonlinear optic, waveguide, piezoelectric, and pyroelectric materials and devices. Diacetylenes which are crystallizable into crystals having a non-centrosymmetric unit cell may form single crystals or, if they do not, may possibly be elaborated into a polar thin film upon a substrate by the Langmuir-Blodgett technique. Such films often may be polymerized either thermally or by irradiation for use in nonlinear optical systems. Diacetylenes are covalently bonded to substrates through employment of silane species and subsequently polymerized to yield nonlinear optic devices asserted to have high structural integrity in addition to high efficiencies and optical effects.

Other U.S. Pat. Nos. relating to non-linear optical properties of organic materials include U.S. Pat. Nos. 4,807,968; 4,808,332; 4,810,338; 4,818,616; 4,818,802; 4,818,898; 4,818,899; 4,824,219; 4,826,950; 4,822,865; 4,828,758; 4,835,235; 4,839,536; 4,851,270; 4,855,078; 4,855,376; 4,861,129; 4,865,430; 4,867,538; 4,867,540; and 4,868,250.

SUMMARY OF THE INVENTION

This invention provides devices for and method of generating coherent second harmonic light radiation. The devices comprise, in combination, a laser source of coherent light radiation at a fixed fundamental frequency, a crystalline, achiral, straight-chain N-nitrophenyl carbamyl compound that is crystallized in a non-centrosymmetric configuration, means for directing the output radiation of the laser onto the crystalline, achiral, straight-chain N-nitrophenyl carbamyl compound, and output means for utilizing the second harmonic frequency. The non-centrosymmetric, crystalline, achiral, straight-chain N-nitrophenyl carbamyl compound is a derivative of an N-nitrophenyl carbamic acid such that the straight chain is linked to the carbamyl carbon atom by an oxygen atom or nitrogen atom.

This invention also provides achiral, straight-chain, acentrically crystalline, i.e., crystallized in a non-centrosymmetric configuration, N-nitrophenyl carbamyl compounds, that are useful in the aforementioned devices and methods.

This invention further provides crystalline, achiral, straight-chain N-nitrophenyl carbamyl compounds capable of crystallizing in a non-centrosymmetric configuration that are novel per se.

DETAILED DESCRIPTION

Carbamic acid derivatives suitable for devices and method of this invention are characterized as N-nitrophenyl carbamyl compounds derived from straight-chain alcohols or amines, and which may be crystallized in at least one non-centrosymmetric, i.e., acentric, crystalline form. Certain of these N-nitrophenyl carbamyl compounds are novel per se. Crystalline N-nitrophenyl carbamyl compounds suitable for this invention are molecularly achiral species that have no center of symmetry on the crystalline unit cell level. As used herein, the term "straight-chain" means that the molecule has a polymethylene chain containing two or more catenated carbon atoms. The term "non-centrosymmetric" is synonymous with the term "acentric".

N-nitrophenyl carbamyl compounds that have been found to be useful for this invention can be defined by the following two general formulas which depict two major subclasses, namely the ureas (I) and the urethanes (II):

R$^1$HNCONHR$^2$  (I)

R$^1$HNCO$_2$R$^2$  (II)

where $R^1$ represents a nitrophenyl group or a substituted nitrophenyl group, $R^2$ represents a polymethylene group, preferably having 2 to 22 catenated carbon atoms, more preferably 4 to 12 catenated carbon atoms, terminated by $R^3$, where $R^3$ represents a member selected from the group consisting of hydrogen, halogen, unsubstituted ethinyl group, substituted ethinyl group, unsubstituted vinyl group, substituted vinyl group, hydroxy group, alkoxy group, aryloxy group, acyloxy group, alkanesulfonyloxy group, arenesulfonyloxy group, alkanesulfonyl group, arenesulfonyl group, aryloxysulfonyl group, alkylthio group, arylthio group, cyano group, unsubstituted carbonyl, substituted carbonyl group, unsubstituted aryl group, substituted aryl group, unsubstituted amino group, substituted amino group, acyl amino group, and heterocyclic group.

The aforementioned terminal group $R^3$ can contain up to 15 carbon atoms, preferably up to 10 carbon atoms. The nature of the substituents for $R^1$, $R^2$, and $R^3$ is not critical so long as they do not alter the achiral, acentrically crystalline nature of the N-nitrophenyl carbamyl compound. With the exception of those urethane compounds described herein for which $R^3$ is hydrogen, all of these compounds are believed to be novel and are considered a part of this invention. Typically, these novel compounds exhibit more favorable crystallization tendencies and yield less fibrous crystals, i.e., crystals of lower aspect ratio, than those for which $R^3$ is hydrogen; such properties are considered to be advantageous when utilizing these compounds in a second harmonic generator.

Representative examples of N-nitrophenyl carbamyl compounds suitable for use in this invention include those where $R^1$ represents a p-nitrophenyl group, a m-nitrophenyl group, or a substituted nitrophenyl group. Representative examples of N-nitrophenyl carbamyl compounds suitable for use in this invention include those where $R^2$ represents a straight-chain alkyl group such as ethyl, n-butyl, n-pentyl, n-hexyl, n-heptyl, n-octyl, n-nonyl, n-decyl, n-undecyl, n-dodecyl, n-octadecyl, or n-docosyl. Further representative examples include those urethane compounds for which $R^1$ represents a nitrophenyl or substituted nitrophenyl group, preferably a p-nitrophenyl group, and $R^2$ represents a terminally substituted straight-chain alkyl group such as 5-phenylpentyl, 10-undecenyl, 6-fluorohexyl, 6-chlorohexyl, 11-bromoundecyl, 11-iodoundecyl, oleyl (cis-9-octadecenyl), elaidyl (trans-9-octadecenyl), 11-fluoroundecyl, 12-bromododecyl, 11-(phenylethinyl)undecyl, 9-[(phenylethinyl)ethinyl]nonyl, 6-(butylethinyl)hexyl, 8-hydroxyoctyl, 16-bromohexadecyl, and erucyl (cis-13-docosenyl).

Compounds suitable for this invention can be conveniently prepared by well-known methods, such as by reaction of a suitable nitrophenyl isocyanate with an appropriate straight-chain amine or alcohol to provide the resultant urea or urethane, respectively.

Straight-chain amines or alcohols that are preferred for preparation of ureas and urethanes suitable for this invention are those compounds wherein the group $R^2$ has a molecular weight ranging from about 25 to about 300.

Urea and urethane compounds suitable for this invention are substantially transparent to electromagnetic radiation having wavelengths from about 0.5 to about 2 micrometers. Accordingly, urea and urethane compounds of this invention are useful in second harmonic generators wherein both incident radiation and emergent radiation range from about 0.5 micrometer to about 2 micrometers; many of the carbamyl compounds can be used in devices and processes where one wavelength is as low as about 0.4 micrometer, or even somewhat lower.

Generally, urethanes are preferred in a situation where the SHG signal is to be near 0.4 micrometer, and are particularly preferred if the SHG signal is lower than that wavelength, because, other factors being equal, their region of transparency extends slightly further into the ultraviolet region than does that of the ureas. Conversely, ureas are preferred in other situations because their melting points are generally higher than those of urethanes, thereby allowing ureas to be used at higher temperatures and, consequently, at higher levels of laser power.

Devices that are capable of generating coherent second harmonic light radiation with N-nitrophenyl carbamyl compounds described herein are well known in the art. Representative examples of such devices are described in U.S. Pat. Nos. 3,395,329; 3,431,484; 3,858,124; 4,756,598; and 4,818,899; all of which are incorporated herein by reference for the purpose of describing devices that can incorporate the acentrically crystalline N-nitrophenyl carbamyl compounds described herein and exhibit efficient second harmonic generation by means of such incorporation.

Crystals of N-nitrophenyl carbamyl compounds exemplified herein were evaluated for SHG efficiency using the second harmonic generation (SHG) powder test described in Kurtz and Perry, J. Appl. Phys. 39, 3798 (1968). Each sample was crushed (not ground) and sieved. The sample was then mixed with an "index-matching fluid", i.e., a liquid, to minimize scattering, refraction, or phase-incoherence caused by differences in the index of refraction between the particles and the ambient atmosphere. The "index-matched" sample was placed between cell flats, (i.e., windows) spaced $0.35 \pm 0.02$ mm apart. Particles having mean diameters sufficiently small so as to pass through a 180 micrometer screen but sufficiently large so as to be retained by a 75 micrometer screen were used. Each sample was mixed with a drop of "index-matching" fluid (Cargille Scientific Co., Cedar Grove, N.J., n=1.63 or n=1.58 fluids, or n=1.631 polyphenylether described in U.S. Pat. No. 3,034,700). Samples were not index-matched critically, so that the actual SHG efficiencies may be higher than those reported in the examples.

Figure 1:
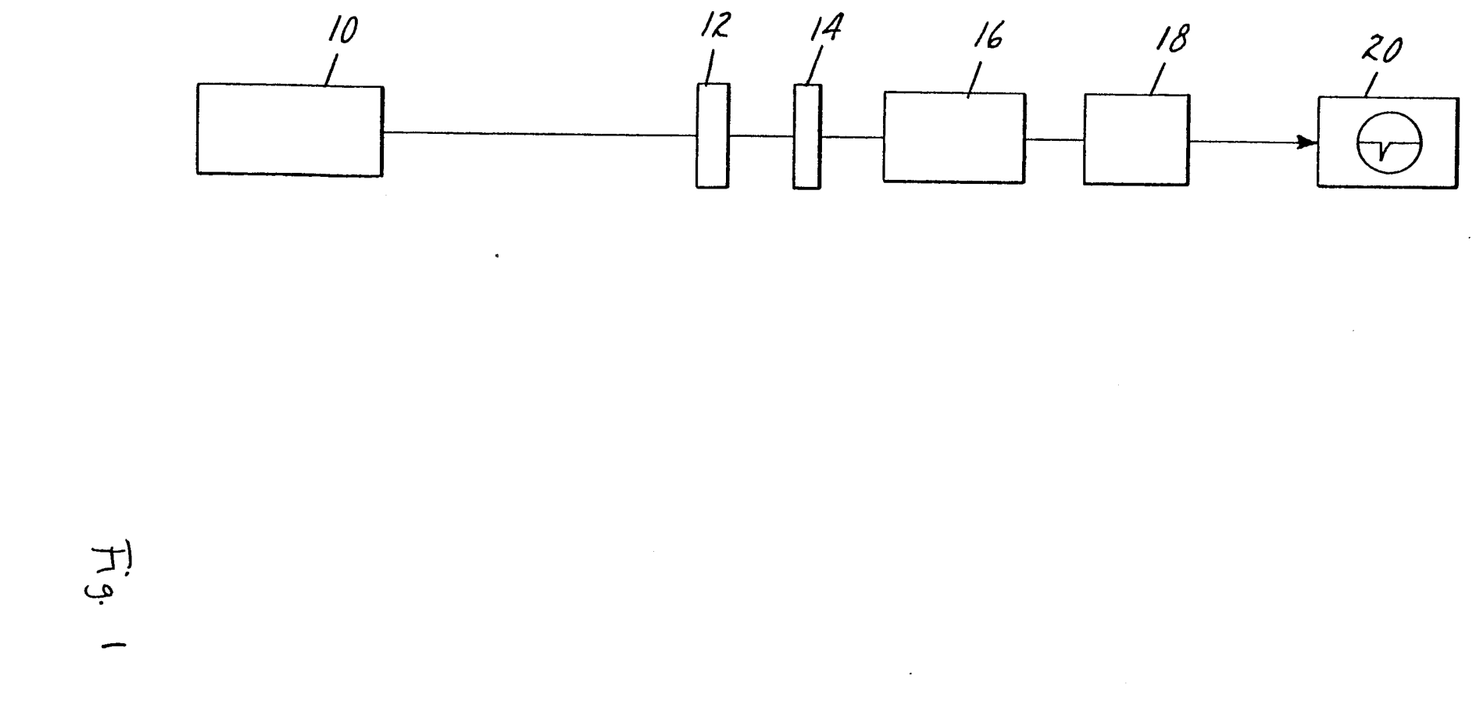
The drawing is a diagrammatic representation of a suitable arrangement for demonstrating the second harmonic generating properties of carbamic acid derivatives of this invention.

Referring now to the drawing, infrared radiation at 1064 nm from a Q-switched Nd-YAG laser 10 was weakly focused onto a cell 12 containing the prepared sample. In the device illustrated in the drawing, the means, e.g., a lens, for directing output radiation of the laser first through a filter 14 (Corning CS2-60 color filter used to block any radiation at 532 nm) and then onto cell 12 containing a sample of N-nitrophenyl carbamyl compound was integrated into laser 10 and is not shown as a separate component. Means for directing the filtered output radiation of the laser onto the sample of N-nitrophenyl carbamyl compound are well-known to one of ordinary skill in the art. An infrared blocking filter 16, placed behind the sample, allowed only second harmonic frequency radiation to pass through a ⅛ meter monochromator 18 tuned at 532 nm. Output of monochromator 18 was directed to a photomultiplier tube 20, and the resulting signal was processed by a boxcar averager 22 that averages over many laser pulses Urea was the chosen standard because of its high second order coefficient, its ready availability, and its wide acceptance in the literature. The urea standard was prepared in the same manner as the samples. It is important to recrystallize the urea to form transparent crystals of a size greater than about 200 micrometers in their smallest dimension, so that the crushed particles made from them will be single crystals rather than polycrystalline masses. The urea standard was index-matched reasonably well, with a mismatch of about 0.01. The reported efficiency of a sample is its SHG signal divided by that of the urea standard measured under the same experimental conditions.

Either or both of two tests can be used to determine non-centrosymmetry or acentricity of crystalline compounds suitable for use in this invention: (1) a pyroelectric test and (2) a piezoelectric test. Alternatively, an absolute method, such as single-crystal x-ray structure determination can be used. In some cases, it is possible to recognize an acentric crystal morphology by classical goniometric microscopic techniques. These latter two methods, where practical, are preferred.

In the pyroelectric test, when an acentric crystal is heated or cooled, it develops electric charges and becomes positive at one end and negative at the other end of its polar axis. Therefore, if a crystal is found to develop electric charges when heated or cooled, it must be concluded that it is non-centrosymmetric.

In the piezoelectric test, when an acentric crystal is compressed or extended in particular directions, it develops electric charges. Conversely, when a potential difference is applied to such a crystal, it expands or contracts. Thus, in an oscillating electric field, the crystal will produce mechanical oscillations which may be detected by suitable transducers. Again, if a crystal is found to thus produce mechanical oscillations, it must be concluded that it is non-centrosymmetric.

Both pyroelectric and piezoelectric tests are well known in the art and are described, for example, in Bunn, C. W., *Chemical Crystallography*, Second ed., Clarendon, Oxford, England, 1961, pp. 321–322, and references therein. "Use of the Pyroelectric Effect To Determine the Absolute Orientation of the Polar Axis in Molecular Crystals," Patil, A. A., Curtin, D. A., and Paul, I. C., J. Am. Chem. Soc. 1985, 107, 726–727, and references therein, also describes a pyroelectric test.

For examples of this invention a modification of the method described by Bunn was employed. This modified method was suitable for detecting moderate to strong pyroelectric behavior. Small crystals of the test material, preferably ca. 0.1 mm in size, are placed in the bowl of a polished stainless steel teaspoon and any charge is removed by means of a 4 millicurie polonium radioactive (alpha particle) source (3M 210 Static Eliminator, 4 inch length, Minnesota Mining and Manufacturing Company, St. Paul, Minn.) held at 1 cm distance for 10 seconds. The bottom of the spoon's bowl is contacted with liquid nitrogen for 40 seconds, thereby creating an electric dipole within each crystal of a non-centrosymmetric material, which polarity is detected by quickly inverting the spoon (in air) and noting adherence of the crystals to the spoon.

Compounds prepared according to the following examples are listed in Tables I-VI and were examined to determine their melting points (m.p.), their sixteen strongest powder x-ray signals for lattice spacings (d-spacings) derived from diffraction angles together with their relative intensities, their pyroelectric test results, and their second harmonic generation efficiencies relative to that of urea. Solvents or mixtures of solvents used for crystallization of the particular compound are also indicated in the aforementioned tables.

The sieved samples were analyzed by x-ray diffraction to establish their powder diffraction patterns, in the exact crystalline state in which the SHG tests were conducted. Unlike the melting point, elemental analysis, NMR, or mass spectra, these diffraction patterns are highly characteristic not only for a particular compound but also for its particular crystal form. It should be understood that relative line intensities may vary systematically due to varying degrees of instrumental resolution or to varying degrees of sample orientation (i.e., non-randomness) on the flat plastic slide which carries the sample into the diffraction apparatus (Automatic Powder Diffractometer, Model No. APD 3600, Philips Electronics Instruments, Inc., Mahwah, N.J.); however, the d-spacings will remain essentially unaffected.

It is necessary to realize that relative line intensity changes may somewhat alter the choice of the sixteen strongest lines, but such changes are extremely unlikely to prevent recognition of identity between two different samples of a compound having the same crystal form.

A more serious challenge to such recognition of sample identity exists as d-spacings become longer, especially above 10 Angstroms, since very small systematic errors in diffraction angle become translated into increasingly larger errors in d-spacing. It is, therefore, especially important to recognize the second and higher orders of diffraction, which result in d-spacings that are precise integral fractions of the longest ones. Inasmuch as these shorter d-spacings may be measured accurately by comparison with those from accepted standard materials, it becomes possible not merely to detect the aforesaid errors, but even to make corrections for them.

With appropriate attention being given to making any such indicated corrections, it is a straightforward matter to compare data gathered on separate and dissimilar x-ray diffractometers, and thus to recognize materials falling within the scope of this invention.

This invention is further illustrated by the following examples, but the particular materials and amounts thereof recited in these examples, as well as other conditions and details, should not be construed to unduly limit this invention.

The following abbreviations were used in the tables following each descriptive example:

| | |
|---|---|
| MeOH | methanol |
| EtOH | ethanol |
| PrOH | n-propanol |
| BuOH | n-butanol |
| BuAc | n-butyl acetate |
| $Et_2O$ | ethyl ether |
| THF | tetrahydrofuran |
| $Me_3C_5H_9$ | 2,2,4-trimethylpentane |
| MeEt | 2-methoxyethanol |
| aq. | aqueous; mixed with water |
| in. | indecisive |

EXAMPLE 1

The following example describes a method of synthesizing a urethane (or carbamate) compound of this invention.

Para-nitrophenyl isocyanate (9 g) was dissolved in anhydrous ether (100 mL). (Corrections must be made for any undissolved yellow solids, specifically bis(p-nitrophenyl)urea, which may be removed by filtration at this point see Example 61). To this solution was added 15 g 11-bromo-1-undecanol (Aldrich Chemical Co.) and 0.5 g dibutyltin dilaurate in ether (120 mL). After the resultant exotherm had subsided, the reaction mixture was warmed to 30°–40° C. for about 2 hours before the yellowish solid product was removed by filtration. The solid was recrystallized from ethanol to give extremely pale yellow crystals in excellent yield (>95%), m.p.=122°–123° C. This product, after crushing and sieving, is reported as Example 1 in Table I. SHG efficiency of this material was sixty-seven times that of the standard urea sample when measured by the method of Kurtz and Perry.

Compounds of Examples 2 through 60, inclusive, were prepared in substantially the same manner as was the compound of Example 1.

TABLE I $$ROCNH-\underset{}{\bigcirc}-NO_2$$

| Example number | R | Crystallization solvent | Melting point (°C.) | Pyroelectric test | SHG efficiency |
|---|---|---|---|---|---|
| 1 | Br(CH$_2$)$_{11}$— | EtOH | 123 | + | 67 |
| 2 | C$_2$H$_5$— | EtOH (hot) | 128$^a$ | + | 23 |
| 3 | n-C$_3$H$_7$— | n-PrOH | 117$^a$ | — | 0.000 |
| 4 | n-C$_4$H$_9$ | n-BuOH | 96$^a$ | + | 85 |
| 5 | n-C$_5$H$_{11}$— | EtOH (hot aq.) | 93$^a$ | + | 46 |
| 6 | n-C$_6$H$_{13}$— | EtOH | 104$^a$ | + | 154; High$^b$ |
| 7 | n-C$_7$H$_{15}$— | EtOH | 104$^a$ | + | 110 |
| 8 | n-C$_8$H$_{17}$— | EtOH | 111$^a$ | + | 62 |
| 9 | n-C$_9$H$_{19}$— | EtOH | 108$^a$ | + | 80 |
| 10 | n-C$_{10}$H$_{21}$— | EtOH | 114$^a$ | + | 99 |
| 11 | n-C$_{11}$H$_{23}$— | EtOH | 112$^a$ | + | 20 |
| 12 | n-C$_{12}$H$_{25}$— | EtOH | 118$^a$ | + | 8 |
| 13 | n-C$_{13}$H$_{27}$— | n-C$_7$H$_{16}$ | 115 | + | 7.6 |
| 14 | CH$_3$— | MeOH | 179$^a$ | — | 0.001 |
| 15 | HC≡C(CH$_2$)$_9$— | EtOH | 114 | + | 32 |
| 16 | n-C$_{16}$H$_{33}$— | EtOH | 120$^a$ | + | 2.9 |
| 17 | C$_6$H$_5$(CH$_2$)$_5$— | EtOH | 74 | + | 9 |
| 18 | n-C$_{18}$H$_{37}$ | CH$_2$Cl$_2$ | 122$^a$ | + | 14 |
| 19 | n-C$_{19}$H$_{39}$— | EtOH | 120 | + | 0.5 |
| 20 | Cl(CH$_2$)$_6$— | n-PrOH | 89 | + | 24 |
| 21 | I(CH$_2$)$_{11}$— | EtOH | 129 | + | 17 |
| 22 | n-C$_{22}$H$_{45}$— | EtOH | 124 | + | 0.6 |
| 23 | cis-n-C$_8$H$_{17}$—CH=CH(CH$_2$)$_8$— | EtOH | 93 | + | 0.5 |
| 24 | Br(CH$_2$)$_{12}$— | EtOH | 102 | + | 44 |
| 25 | Br(CH$_2$)$_{16}$— | EtOH | 111 | + | 23 |
| 26 | n-C$_7$H$_{15}$— | EtOH | 104$^a$ | + | 0.007 |
| 27 | n-C$_7$H$_{15}$— | n-BuAc | 105$^a$ | in. | 0.4 |
| 28 | n-C$_7$H$_{15}$— | EtOH | 103$^a$ | + | 0.4 |
| 29 | n-C$_7$H$_{15}$— | Et$_2$O | 104$^a$ | + | 0.6 |
| 30 | n-C$_9$H$_{19}$— | EtOH | 107$^a$ | + | 13 |
| 31 | n-C$_{11}$H$_{23}$— | n-C$_7$H$_{16}$ | 111$^a$ |  | 13 |
| 32 | n-C$_{16}$H$_{33}$— | n-C$_7$H$_{16}$ | 121$^a$ | + | 60 |
| 33 | n-C$_{18}$H$_{37}$— | THF | 120$^a$ |  | 5 |
| 34 | Br(CH$_2$)$_{11}$— | EtOH | 123 |  | 33 |
| 35 | Br(CH$_2$)$_{11}$— | Acetone | 123 |  | 37 |
| 36 | n-C$_{13}$H$_{27}$— | EtOH | 117 | + | 7.1 |
| 37 | CH$_2$=CH(CH$_2$)$_9$— | n-C$_7$H$_{16}$ | 103 | + | 0.8 |
| 38 | Cl(CH$_2$)$_6$— | EtOH | 89 | + | 18 |
| 39 | n-C$_5$H$_{11}$— | EtOH (cool aq.) | 93$^a$ | in. | 0.03 |
| 40 | n-C$_{22}$H$_{45}$— | EtOH | 124 | + | 0.4 |
| 41 | Br(CH$_2$)$_{16}$— | EtOH | 110 | + | 0.6 |
| 42 | CH$_2$=CH(CH$_2$)$_9$— | EtOH | 104 | + | 0.8 |
| 43 | cis-n-C$_8$H$_{17}$CH=CH—(CH$_2$)$_{12}$— | Me$_3$C$_5$H$_9$ | 80 | + | 3.6 |
| 44 | C$_2$H$_5$— | EtOH (cool) | 130$^a$ | + | 5.5 |
| 45 | CH$_3$S(CH$_2$)$_2$— | EtOH (aq.) | 75 | + | 18 |
| 46 | C$_6$H$_5$O(CH$_2$)$_2$— | EtOH (aq.) | 98 | + | 1.3 |
| 47 | N≡C(CH$_2$)$_2$— | EtOH (hot) | 167 | in. | 0.02 |
| 48 | n-C$_3$H$_7$— | EtOH (hot aq.) | 117$^a$ | — | 0.000 |
| 49 | HO(CH$_2$)$_8$— | EtOH (aq.) | 116 | + | 10 |
| 50 | p-O$_2$NC$_6$H$_4$NHCO$_2$—(CH$_2$)$_8$— | EtOH | 217 | + | 0.004 |
| 51 | CH$_3$CO$_2$(CH$_2$)$_8$— | MeEt | 128 | + | 0.002 |
| 52 | n-C$_7$H$_{15}$— | EtOH (hot) | 104$^a$ | + | Good$^b$ |

$^a$Melting points for these compounds have been reported previously in scientific literature. Because of higher material purity, the listed melting points are on average more than 2° C. higher than the values previously reported in scientific literature. The melting points reported herein were measured on apparatus calibrated to the International Temperature Scale of 1990.
$^b$Observing visually as a bright green luminosity when irradiated by a Nd-YAG laser emitting at 1.064μ wavelength.

TABLE II

| Example |

TABLE II-continued

| Number | d | i | d | i | d | i | d | i | d | i | d | i | d | i | d | i |
|---|---|---|---|---|---|---|---|---|---|---|---|---|---|---|---|---|
| 1 | 15.55 | 100 | 10.42 | 87 | 4.74 | 45 | 4.54 | 29 | 4.16 | 53 | 3.89 | 42 | 3.80 | 91 | 3.63 | 62 |
| 2 | 16.68 | 100 | 8.21 | 34 | 6.29 | 6 | 5.82 | 21 | 4.88 | 61 | 4.01 | 49 | 3.83 | 13 | 3.68 | 16 |
| 3 | 9.96 | 2.5 | 5.32 | 1.4 | 4.92 | 1.7 | 4.53 | 2.2 | 4.11 | 4.6 | 3.73 | 4.3 | 3.66 | 2.2 | 3.59 | 2.4 |
| 4 | 18.00 | 100 | 9.06 | 38 | 5.34 | 32 | 4.74 | 90 | 4.46 | 18 | 4.22 | 10 | 4.08 | 26 | 3.94 | 9 |
| 5 | 21.61 | 100 | 10.82 | 10 | 5.38 | 3 | 5.22 | 4 | 4.91 | 7 | 4.29 | 4 | 4.02 | 2 | 3.83 | 6 |
| 6 | 20.91 | 100 | 10.69 | 29 | 5.35 | 15 | 5.24 | 18 | 4.71 | 50 | 4.25 | 6 | 4.13 | 23 | 3.90 | 12 |
| 7 | 24.72 | 100 | 12.22 | 4 | 6.05 | 3 | 5.29 | 7 | 4.79 | 28 | 4.26 | 5 | 4.12 | 5 | 3.99 | 6 |
| 8 | 24.38 | 100 | 12.44 | 2.4 | 8.27 | 1.5 | 6.17 | 7 | 5.21 | 7 | 4.73 | 20 | 4.21 | 10 | 4.09 | 11 |
| 9 | 26.57 | 95 | 6.75 | 28 | 5.19 | 20 | 4.76 | 100 | 4.47 | 19 | 4.29 | 24 | 3.89 | 41 | 3.82 | 33 |
| 10 | 27.74 | 100 | 6.94 | 24 | 5.15 | 6 | 4.71 | 19 | 4.60 | 21 | 4.25 | 10 | 3.94 | 14 | 3.57 | 21 |
| 11 | 30.05 | 100 | 7.56 | 32 | 5.15 | 8 | 5.02 | 10 | 4.77 | 36 | 4.34 | 11 | 4.28 | 6 | 4.11 | 6 |
| 12 | 30.50 | 100 | 7.64 | 24 | 5.16 | 8 | 5.07 | 7 | 4.77 | 25 | 4.34 | 9 | 4.14 | 3 | 3.78 | 30 |
| 13 | 33.54 | 100 | 8.39 | 26 | 5.57 | 7 | 5.10 | 18 | 4.75 | 93 | 4.36 | 23 | 4.15 | 13 | 3.95 | 8 |
| 14 | 8.32 | 3.0 | 8.23 | 2.8 | 7.10 | 3.1 | 6.40 | 11 | 4.66 | 10 | 4.09 | 2.5 | 3.57 | 5 | 3.482 | 1.2 |
| 15 | 28.48 | 60 | 7.10 | 24 | 5.08 | 32 | 4.86 | 53 | 4.71 | 34 | 4.64 | 34 | 4.21 | 22 | 3.76 | 55 |
| 16 | 37.47 | 52 | 18.60 | 47 | 12.47 | 12 | 9.41 | 52 | 6.27 | 24 | 5.04 | 32 | 4.70 | 87 | 4.36 | 45 |
| 17 | 26.63 | 100 | 5.00 | 31 | 4.78 | 51 | 4.53 | 26 | 4.37 | 33 | 4.31 | 30 | 4.06 | 30 | 3.97 | 26 |
| 18 | 40.63 | 75 | 20.32 | 35 | 13.53 | 14 | 10.15 | 21 | 6.78 | 15 | 5.50 | 4 | 5.00 | 43 | 4.69 | 100 |
| 19 | 42.99 | 100 | 21.35 | 34 | 14.33 | 45 | 10.80 | 30 | 7.18 | 25 | 5.37 | 8 | 5.00 | 7 | 4.72 | 39 |
| 20 | 7.80 | 17 | 5.13 | 29 | 4.82 | 45 | 4.51 | 17 | 3.95 | 41 | 3.88 | 100 | 3.79 | 24 | 3.59 | 12 |
| 21 | 16.62 | 87 | 16.37 | 100 | 10.94 | 56 | 8.18 | 11 | 6.49 | 14 | 4.27 | 5 | 4.01 | 16 | 3.86 | 5 |
| 22 | 46.58 | 40 | 23.21 | 26 | 15.58 | 18 | 4.93 | 47 | 4.66 | 94 | 4.40 | 52 | 4.02 | 9 | 3.89 | 16 |
| 23 | 40.65 | 4 | 20.32 | 0.9 | 13.63 | 2.6 | 9.98 | 2.4 | 6.86 | 1.9 | 5.49 | 1.1 | 4.94 | 50 | 4.70 | 100 |
| 24 | 33.43 | 5 | 16.71 | 100 | 11.14 | 31 | 6.69 | 7 | 4.89 | 4 | 4.73 | 22 | 4.35 | 9 | 4.30 | 10 |
| 25 | 19.30 | 100 | 13.06 | 46 | 7.91 | 65 | 4.91 | 20 | 4.84 | 13 | 4.67 | 85 | 4.36 | 42 | 4.24 | 18 |
| 26 | 23.77 | 100 | 5.13 | 12 | 5.00 | 12 | 4.87 | 9 | 4.74 | 1 | 4.22 | 12 | 3.98 | 11 | 3.86 | 18 |
| 27 | 23.66 | 100 | 11.94 | 12 | 5.98 | 10 | 5.10 | 8 | 4.99 | 8 | 4.86 | 6 | 4.73 | 13 | 4.21 | 10 |
| 28 | 24.32 | 100 | 12.15 | 14 | 5.12 | 18 | 5.00 | 19 | 4.74 | 26 | 4.22 | 14 | 3.98 | 15 | 3.85 | 18 |
| 30 | 27.69 | 33 | 6.73 | 29 | 5.17 | 21 | 4.75 | 100 | 4.45 | 21 | 4.28 | 26 | 3.88 | 45 | 3.81 | 40 |
| 32 | 37.67 | 100 | 18.81 | 12 | 9.45 | 9 | 6.28 | 3 | 5.06 | 14 | 4.72 | 36 | 4.37 | 19 | 3.87 | 10 |
| 36 | 33.01 | 80 | 8.33 | 50 | 5.55 | 11 | 5.09 | 19 | 4.74 | 100 | 4.36 | 27 | 4.14 | 23 | 3.94 | 29 |
| 37 | 30.15 | 100 | 7.45 | 5 | 5.15 | 3 | 4.91 | 2.5 | 4.71 | 4 | 4.27 | 2.6 | 3.88 | 1.6 | 3.69 | 6 |
| 38 | 5.14 | 46 | 4.83 | 72 | 4.53 | 27 | 4.22 | 15 | 3.97 | 57 | 3.89 | 100 | 3.82 | 74 | 3.69 | 21 |
| 39 | 22.00 | 100 | 10.86 | 13 | 5.33 | 4 | 5.06 | 6 | 4.90 | 3.4 | 4.23 | 3.5 | 4.01 | 6 | 3.87 | 7 |
| 43 | 49.57 | 100 | 24.75 | 24 | 16.50 | 18 | 12.01 | 3 | 8.17 | 8 | 7.16 | 2 | 6.38 | 1 | 5.34 | 8 |
| 44 | 16.03 | 100 | 8.10 | 39 | 6.21 | 8 | 5.77 | 27 | 4.84 | 72 | 3.98 | 59 | 3.80 | 10 | 3.66 | 13 |
| 45 | 19.05 | 100 | 9.43 | 20 | 5.14 | 76 | 4.68 | 54 | 3.77 | 5 | 3.63 | 8 | 3.56 | 19 | 3.307 | 37 |
| 46 | 15.99 | 26 | 7.86 | 11 | 6.30 | 10 | 5.97 | 10 | 4.90 | 11 | 4.71 | 9 | 4.60 | 26 | 4.34 | 15 |
| 47 | 9.18 | 21 | 7.10 | 31 | 6.16 | 20 | 4.39 | 100 | 3.65 | 19 | 3.62 | 16 | 3.423 | 61 | 3.319 | 18 |
| 48 | 9.93 | 6 | 5.31 | 1.9 | 4.95 | 3 | 4.56 | 3 | 4.13 | 6 | 3.74 | 6 | 3.67 | 2.0 | 3.62 | 2.2 |
| 49 | 25.89 | 100 | 8.57 | 8 | 6.42 | 1.4 | 5.14 | 1.3 | 5.02 | 1.4 | 4.82 | 3 | 4.28 | 4 | 4.15 | 1.7 |
| 52 | 23.90 | 100 | 11.84 | 5 | 5.96 | 4 | 4.75 | 2.3 | 4.22 | 1.1 | 3.97 | 7 | 3.86 | 1.7 | 3.72 | 1.4 |

| Example number | D | I | D | I | D | I | D | I | D | I | D | I | D | I | D | I |
|---|---|---|---|---|---|---|---|---|---|---|---|---|---|---|---|---|
| 1 | 3.61 | 43 | 3.52 | 24 | 3.475 | 50 | 3.333 | 49 | 3.194 | 24 | 2.595 | 26 | 2.355 | 23 | 2.227 | 23 |
| 2 | 3.54 | 52 | 3.331 | 4 | 3.175 | 30 | 1.141 | 27 | 2.661 | 7 | 2.491 | 5 | 2.460 | 8 | 2.185 | 3.4 |
| 3 | 3.450 | 100 | 3.200 | 1.5 | 3.150 | 1.4 | 2.949 | 1.3 | 2.849 | 1.1 | 2.777 | 3.7 | 2.644 | 1.3 | 2.000 | 1.1 |
| 4 | 3.68 | 42 | 3.57 | 93 | 3.496 | 9 | 3.334 | 60 | 3.065 | 19 | 2.980 | 20 | 2.411 | 10 | 2.027 | 6 |
| 5 | 3.63 | 6 | 3.56 | 5 | 3.500 | 5 | 3.356 | 10 | 3.204 | 1.5 | 3.058 | 3 | 2.432 | 1.5 | 2.162 | 1.1 |
| 6 | 3.84 | 6 | 3.62 | 16 | 3.55 | 26 | 3.421 | 41 | 3.345 | 16 | 3.057 | 9 | 2.545 | 5 | 2.133 | 6 |
| 7 | 3.91 | 6 | 3.73 | 13 | 3.66 | 19 | 3.498 | 13 | 3.413 | 2.4 | 3.252 | 15 | 2.984 | 3 | 2.452 | 1.2 |
| 8 | 3.78 | 2.7 | 3.71 | 8 | 3.57 | 4 | 3.50 | 2.3 | 3.323 | 12 | 3.069 | 3.4 | 2.459 | 3.3 | 1.887 | 1.3 |
| 9 | 3.64 | 37 | 3.51 | 86 | 3.431 | 40 | 3.351 | 12 | 3.203 | 38 | 3.170 | 26 | 2.981 | 16 | 2.241 | 9 |
| 10 | 3.52 | 5 | 3.448 | 19 | 3.298 | 3 | 3.232 | 9 | 3.071 | 3.1 | 2.299 | 7 | 2.131 | 4 | 1.840 | 5 |
| 11 | 3.76 | 50 | 3.60 | 12 | 3.420 | 38 | 3.201 | 11 | 3.127 | 5 | 3.002 | 7 | 2.500 | 5 | 2.143 | 5 |
| 12 | 3.61 | 6 | 3.437 | 21 | 3.358 | 3 | 3.224 | 5 | 3.148 | 3 | 3.023 | 4 | 2.508 | 2.0 | 2.156 | 2.4 |
| 13 | 3.84 | 5 | 3.70 | 14 | 3.63 | 26 | 3.55 | 7 | 3.341 | 17 | 3.186 | 8 | 2.181 | 4 | 2.061 | 4 |
| 14 | 3.312 | 8 | 3.216 | 100 | 3.150 | 3.1 | 2.626 | 2.2 | 2.588 | 1.9 | 2.491 | 1.5 | 2.200 | 1.4 | 2.095 | 2.2 |
| 15 | 3.61 | 100 | 3.56 | 71 | 3.52 | 53 | 3.464 | 36 | 3.434 | 22 | 3.367 | 32 | 3.148 | 36 | 3.043 | 21 |
| 16 | 4.13 | 13 | 3.86 | 38 | 3.72 | 50 | 3.58 | 100 | 3.419 | 13 | 3.327 | 29 | 3.258 | 18 | 3.098 | 22 |
| 17 | 3.84 | 33 | 3.75 | 33 | 3.68 | 61 | 3.54 | 38 | 3.429 | 58 | 3.308 | 37 | 3.195 | 29 | 3.078 | 32 |
| 18 | 4.37 | 65 | 4.02 | 23 | 3.74 | 12 | 3.66 | 8 | 3.494 | 17 | 3.352 | 8 | 2.238 | 5 | 2.074 | 4 |
| 19 | 4.42 | 14 | 4.27 | 18 | 3.87 | 26 | 3.70 | 8 | 3.62 | 54 | 3.56 | 16 | 3.400 | 21 | 2.086 | 10 |
| 20 | 3.437 | 30 | 3.409 | 9 | 3.352 | 13 | 3.236 | 37 | 2.918 | 17 | 2.645 | 9 | 2.394 | 8 | 2.340 | 20 |
| 21 | 3.278 | 6 | 3.199 | 17 | 2.908 | 11 | 2.667 | 16 | 2.460 | 6 | 2.282 | 17 | 2.132 | 6 | 1.880 | 8 |
| 22 | 3.79 | 85 | 3.70 | 50 | 3.57 | 100 | 3.466 | 19 | 3.345 | 28 | 3.210 | 18 | 3.081 | 12 | 2.484 | 10 |
| 23 | 4.31 | 36 | 3.60 | 78 | 2.804 | 3.0 | — | — | — | — | — | — | — | — | — | — |
| 24 | 4.14 | 15 | 3.95 | 9 | 3.86 | 5 | 3.79 | 6 | 3.72 | 4 | 3.63 | 22 | 3.381 | 5 | 3.314 | 9 |
| 25 | 3.93 | 66 | 3.85 | 27 | 3.70 | 85 | 3.58 | 19 | 3.53 | 14 | 3.444 | 27 | 3.338 | 18 | 3.274 | 26 |
| 26 | 3.77 | 12 | 3.73 | 13 | 3.65 | 17 | 3.54 | 21 | 3.442 | 23 | 3.371 | 15 | 3.341 | 20 | 3.188 | 14 |
| 27 | 3.96 | 19 | 3.85 | 14 | 3.73 | 10 | 3.64 | 15 | 3.53 | 20 | 3.434 | 17 | 3.332 | 19 | 3.181 | 12 |
| 28 | 3.77 | 14 | 3.73 | 19 | 3.64 | 20 | 3.53 | 21 | 3.436 | 26 | 3.373 | 13 | 3.337 | 18 | 3.183 | 16 |
| 30 | 3.64 | 41 | 3.51 | 88 | 3.422 | 43 | 3.347 | 17 | 3.197 | 42 | 2.977 | 16 | 2.242 | 9 | 2.081 | 7 |
| 32 | 3.73 | 11 | 3.60 | 27 | 3.431 | 4 | 3.340 | 7 | 3.263 | 4 | 3.108 | 5 | 2.524 | 3 | 2.151 | 3 |
| 36 | 3.83 | 13 | 3.69 | 39 | 3.62 | 91 | 3.54 | 23 | 3.343 | 57 | 3.185 | 22 | 3.001 | 12 | 2.183 | 10 |
| 37 | 3.66 | 5 | 3.53 | 1.4 | 3.436 | 0.5 | 3.360 | 1.2 | 3.323 | 1.0 | 3.214 | 1.4 | 3.114 | 1.0 | 2.441 | 0.7 |
| 38 | 3.60 | 40 | 3.487 | 80 | 3.425 | 23 | 3.361 | 36 | 3.251 | 83 | 3.199 | 21 | 2.926 | 15 | 2.342 | 5 |
| 39 | 3.82 | 5 | 3.70 | 2.6 | 3.63 | 6 | 3.51 | 9 | 3.425 | 11 | 3.345 | 5 | 3.282 | 2.9 | 3.053 | 5 |
| 43 | 4.80 | 33 | 4.44 | 6 | 4.39 | 7 | 4.10 | 4 | 3.76 | 14 | 3.56 | 23 | 3.419 | 22 | — | — |
| 44 | 3.55 | 24 | 3.52 | 39 | 3.156 | 35 | 3.124 | 26 | 2.650 | 11 | 2.479 | 9 | 2.450 | 12 | 2.204 | 5 |

TABLE II-continued

| 45 | 3.244 | 5   | 3.113 | 38 | 3.081 | 23  | 2.689 | 8   | 2.410 | 4   | 2.378 | 4   | 2.333 | 5   | 1.864 | 13  |
| -- | ----- | --- | ----- | -- | ----- | --- | ----- | --- | ----- | --- | ----- | --- | ----- | --- | ----- | --- |
| 46 | 4.08  | 14  | 3.96  | 81 | 3.91  | 47  | 3.60  | 30  | 3.55  | 10  | 3.354 | 9   | 3.188 | 100 | 2.656 | 8   |
| 47 | 3.272 | 21  | 3.134 | 81 | 3.056 | 15  | 2.699 | 16  | 2.571 | 31  | 2.198 | 51  | 1.957 | 16  | 1.924 | 14  |
| 48 | 3.476 | 100 | 3.390 | 3  | 3.212 | 1.5 | 3.165 | 1.3 | 2.960 | 1.8 | 2.857 | 1.2 | 2.786 | 4   | 2.656 | 1.3 |
| 49 | 3.85  | 8   | 3.81  | 6  | 3.65  | 13  | 3.379 | 1.5 | 3.265 | 3   | 3.140 | 1.7 | 2.328 | 1.4 | 2.079 | 1.7 |
| 52 | 3.64  | 3   | 3.53  | 3  | 3.435 | 2.0 | 3.394 | 2.2 | 3.330 | 2.5 | 3.239 | 1.2 | 3.181 | 1.4 | 2.382 | 1.1 |

TABLE III

| Example number | R | A | B | C | Crystallization solvent | Melting point (°C.) | Pyroelectric test | SHG efficiency |
| --- | --- | --- | --- | --- | --- | --- | --- | --- |
| 53 | $Cl(CH_2)_6-$ | $CH_3$ | H | $NO_2$ | EtOH | 101 | — | 0.000 |
| 54 | $Cl(CH_2)_6-$ | $OCH_3$ | H | $NO_2$ | EtOH | 91 | — | 0.000 |
| 55 | $Cl(CH_2)_6-$ | $OCH_3$ | H | $NO_2$ | $Et_2O$ | 91 | — | 0.000 |
| 56 | $Br(CH_2)_{11}-$ | H | $NO_2$ | H | EtOH | 78 | + | 0.05 |
| 57 | $Br(CH_2)_{11}-$ | Cl | H | $NO_2$ | EtOH | 73 | + | 0.06 |
| 58 | $Br(CH_2)_{11}-$ | $CH_3$ | H | $NO_2$ | EtOH | 83 | — | 0.02 |
| 59 | $Br(CH_2)_{11}-$ | $OCH_3$ | H | $NO_2$ | EtOH | 96 | +[a] | 0.34 |
| 60 | $Cl(CH_2)_6-$ | Cl | H | $NO_2$ | EtOH | 73 | — | 0.001 |
| 60A[b] | $Cl(CH_2)_6-$ | Cl | H | $NO_2$ | EtOH | | | |

[a] Very fine crystals were clinging together in balls which fell off the spoon; this was attributed to acentric polarity.
[b] Example 60A is a single crystal taken from Example 60 and subjected to single-crystal x-ray structure analysis, from which data the x-ray powder diffraction pattern was computed. The resulting positions and relative intensities of the matching peaks are shown in Table IV below; no discrepant peaks were found. This cyrstal form was found to have a center of symmetry and thus was not acentric, confirming the result of the pyroelectric test performed for Example 60.

TABLE IV

| Example number | D | I | D | I | D | I | D | I | D | I | D | I | D | I | D | I |
| --- | --- | --- | --- | --- | --- | --- | --- | --- | --- | --- | --- | --- | --- | --- | --- | --- |
| 53 | 9.91 | 7 | 8.44 | 11 | 5.79 | 15 | 5.17 | 34 | 4.49 | 19 | 4.04 | 78 | 4.02 | 65 | 3.87 | 100 |
| 54 | 10.29 | 12 | 7.31 | 10 | 5.81 | 7 | 4.35 | 6 | 4.24 | 4 | 4.08 | 7 | 3.91 | 17 | 3.76 | 100 |
| 56 | 19.32 | 40 | 9.51 | 14 | 4.86 | 25 | 4.51 | 33 | 4.27 | 23 | 4.17 | 42 | 4.02 | 29 | 3.98 | 17 |
| 57 | 21.86 | 100 | 6.30 | 18 | 4.90 | 11 | 4.48 | 28 | 4.38 | 13 | 4.28 | 14 | 4.16 | 27 | 4.08 | 11 |
| 58 | 12.40 | 11 | 8.59 | 7 | 6.58 | 23 | 6.34 | 19 | 4.41 | 10 | 4.08 | 6 | 3.96 | 100 | 3.54 | 7 |
| 59 | 18.03 | 21 | 11.87 | 54 | 7.08 | 14 | 4.94 | 34 | 4.48 | 100 | 4.40 | 15 | 4.07 | 39 | 4.00 | 19 |
| 60 | 8.50 | 18 | 5.14 | 24 | 4.95 | 6 | 4.02 | 71 | 3.84 | 36 | 3.82 | 100 | 3.78 | 89 | 3.53 | 36 |
| 60A[a] | 8.495 | 24 | 5.143 | 19 | 4.924 | 8 | 4.014 | 46 | 3.865 | 11 | 3.808 | 100 | 3.764 | 59 | 3.556 | 12 |
|  |  |  |  |  |  |  |  |  |  |  |  |  |  |  | 3.514 | 16 |

| Example number | D | I | D | I | D | I | D | I | D | I | D | I | D | I | D | I |
| --- | --- | --- | --- | --- | --- | --- | --- | --- | --- | --- | --- | --- | --- | --- | --- | --- |
| 53 | 3.82 | 74 | 3.57 | 15 | 3.321 | 45 | 3.248 | 29 | 3.234 | 22 | 2.991 | 31 | 2.886 | 13 | 2.293 | 13 |
| 54 | 3.65 | 5 | 3.56 | 11 | 3.410 | 9 | 3.118 | 5 | 3.078 | 8 | 2.889 | 9 | 2.837 | 7 | 2.684 | 8 |
| 56 | 3.92 | 100 | 3.78 | 26 | 3.58 | 14 | 3.407 | 40 | 3.347 | 15 | 2.970 | 15 | 2.689 | 17 | 2.139 | 17 |
| 57 | 3.75 | 16 | 3.53 | 40 | 3.381 | 28 | 3.200 | 12 | 3.118 | 12 | 3.061 | 12 | 3.034 | 14 | 2.800 | 18 |
| 58 | 3.470 | 60 | 3.305 | 11* | 3.283 | 15 | 3.253 | 18 | 3.091 | 7 | 2.598 | 23 | 2.481 | 7 | 2.287 | 5 |
| 59 | 3.82 | 49 | 3.71 | 15 | 3.61 | 17 | 3.53 | 15 | 3.436 | 81 | 3.278 | 15 | 3.193 | 18 | 2.698 | 14 |
| 60 | 3.280 | 47 | 3.203 | 20 | 3.036 | 4 | 2.980 | 6 | 2.859 | 8 | 2.558 | 9 | 2.485 | 4 | 2.075 | 4 |
| 60A[a] | 3.275 | 46 | 3.190 | 9 | 3.036 | 2 | 2.973 | 6 | 2.887 | 3 | 2.571 | 2 | 2.481 | 3 | 2.066 | 3 |
|  |  |  |  |  | 3.019 | 2 |  |  | 2.845 | 3 | 2.550 | 5 |  |  |  |  |
|  |  |  |  |  |  |  |  |  |  |  | 2.543 | 5 |  |  |  |  |

[a] Multiple computed lines are shown for Example 60A; it was judged that such closely spaced lines had not been resolved experimentally.

EXAMPLE 61

The following example describes a method of synthesizing a urea compound (N-octadecyl-N'-p-nitrophenyl urea) suitable for this invention.

Because ostensibly pure p-nitrophenyl isocyanate may contain sizable proportions of its hydrolysis product, bis-(p-nitrophenyl)-urea, it is often necessary to repurify the p-nitrophenyl isocyanate by dissolving it in warm toluene (or in ether) and removing the urea by filtration. Repurified isocyanate crystallizes upon evaporation of toluene (or ether) from the tepid solution.

N-Octadecylamine (Aldrich Chemical Co., Milwaukee, Wis.)(1.35 g, 0.005 mole) and freshly repurified p-nitrophenyl isocyanate (Eastman Chemical Co., Rochester, N.Y.)(0.83 g, 0.005 mole) were dissolved in a total of 25 mL toluene and mixed in a 50 mL Erlenmeyer flask fitted with air condenser. The resulting mixture was heated for about two hours on a steam bath. A yellowish precipitate formed and was collected by filtration, washed with toluene and dried; the solid weighed 1.94 g (theor. 2.18 g) and had a melting point of 119°-121° C. The precipitate was dissolved in 40 mL boiling acetone and crystallized upon cooling. After filtration, washing with about 20 mL acetone, and drying, a white solid was recovered (1.29 g, m.p. 120°-122° C.). An additional 0.30 g, m.p. 120°-121° C., was recovered from the filtrate. This product, after crushing and sieving, is reported as Example 61 in Table II; its SHG efficiency was five times that of the standard urea sample when measured by the method of Kurtz and Perry.

Compounds of Examples 62 through 80, inclusive, were prepared in substantially the same manner as was the compound of Example 61, though often with anhydrous ether rather than toluene as the reaction solvent.

TABLE V

| Example number | R | Crystallization solvent | Melting point (°C.) | Pyroelectric test | SHG efficiency |
|---|---|---|---|---|---|
| 61 | n-$C_{18}H_{37}$— | Acetone | 122 | + | 5 |
| 62 | $HO_2C(CH_2)_{10}$— | EtOH | 184[b] | — | 0.00 |
| 63 | O=C—$(CH_2)_3$—N—$(CH_2)_3$— | EtOH | 172 | — | 0.004 |
| 64 | $(CH_3)_2N(CH_2)_3$— | EtOH | 90 | in. | 0.03 |
| 65 | n-$C_5H_{11}$— | EtOH | 131 | in. | 0.001 |
| 66 | n-$C_6H_{13}$— | n-$C_6H_{13}NH_2$ | 112 | + | 0.9 |
| 67 | n-$C_{10}H_{21}$— | EtOH | 118 | + | 38 |
| 68 | n-$C_{12}H_{25}$— | EtOH | 118 | + | 8 |
| 69 | n-$C_{14}H_{29}$— | EtOH | 121 | + | 11 |
| 70 | n-$C_{16}H_{33}$— | EtOH | 120 | + | 6 |
| 71 | trans-$C_8H_{17}CH=CH$—$(CH_2)_8$— | EtOH | 105 | + | 1.6 |
| 72 | n-$C_{18}H_{37}$— | THF | 123 | + | 0.9 |
| 73 | n-$C_{18}H_{37}$— | $CH_2Cl_2$ | 123 | — | 0.000 |
| 74 | n-$C_{18}H_{37}$— | $CH_2Cl_2$ | 122 | — | 0.002 |
| 75 | n-$C_{18}H_{37}$— | THF | 121 | — | 0.000 |
| 76 | n-$C_{18}H_{37}$— | Acetone | 121 | + | 3 |
| 77 | n-$C_{10}H_{21}$— | EtOH | 118 | + | 3 |
| 78 | n-$C_{18}H_{37}$— | $CH_2Cl_2$ | 122 | + | 14 |
| 79 | n-$C_5H_{11}$— | Acetone + $Me_3C_5H_9$ | 133 | + | 0.003 |
| 80 | n-$C_{12}H_{25}$—[a] | Toluene | 98 | + | 0.004 |

[a] Aryl group is 2-chloro-4-nitrophenyl
[b] Melted with decomposition

TABLE VI

| Example number | d | i | d | i | d | i | d | i | d | i | d | i | d | i | d | i |
|---|---|---|---|---|---|---|---|---|---|---|---|---|---|---|---|---|
| 61 | 41.54 | 100 | 20.66 | 8 | 4.69 | 21 | 4.64 | 25 | 4.45 | 40 | 4.23 | 46 | 4.08 | 28 | 3.95 | 66 |
| 62 | 19.26 | 42 | 18.68 | 23 | 4.97 | 19 | 4.60 | 20 | 4.17 | 25 | 4.10 | 23 | 3.97 | 70 | 3.89 | 23 |
| 63 | 9.11 | 9 | 6.48 | 9 | 5.99 | 13 | 5.50 | 11 | 4.89 | 57 | 4.56 | 8 | 4.30 | 30 | 3.96 | 43 |
| 64 | 11.75 | 21 | 9.66 | 32 | 5.50 | 14 | 5.23 | 86 | 4.80 | 25 | 4.62 | 18 | 4.28 | 37 | 4.16 | 11 |
| 65 | 12.34 | 8 | 9.92 | 8 | 8.68 | 12 | 8.56 | 12 | 6.15 | 14 | 5.47 | 16 | 5.34 | 8 | 4.52 | 11 |
| 66 | 22.92 | 100 | 11.26 | 12 | 5.53 | 8 | 4.77 | 5 | 4.58 | 13 | 4.21 | 24 | 3.92 | 24 | 3.74 | 14 |
| 67 | 29.83 | 100 | 7.16 | 9 | 4.75 | 20 | 4.60 | 22 | 4.43 | 12 | 4.23 | 22 | 4.09 | 8 | 3.99 | 41 |
| 68 | 7.95 | 15 | 6.11 | 8 | 4.78 | 4 | 4.65 | 50 | 4.49 | 100 | 4.20 | 20 | 4.01 | 85 | 3.82 | 10 |
| 69 | 34.42 | 75 | 17.11 | 22 | 8.64 | 100 | 5.76 | 31 | 4.58 | 24 | 4.44 | 12 | 4.29 | 28 | 4.23 | 36 |
| 70 | 38.46 | 100 | 19.23 | 8 | 12.84 | 4 | 9.63 | 10 | 6.39 | 5 | 4.68 | 3 | 4.56 | 5 | 4.43 | 4 |
| 71 | 40.66 | 100 | 20.30 | 13 | 13.55 | 15 | 10.19 | 20 | 6.77 | 12 | 4.69 | 41 | 4.46 | 63 | 4.23 | 82 |
| 72 | 41.26 | 100 | 20.63 | 12 | 13.77 | 6 | 10.34 | 8 | 7.47 | 3 | 6.85 | 5 | 4.62 | 3 | 4.52 | 5 |
| 73 | 25.02 | 11 | 12.55 | 8 | 12.35 | 8 | 8.25 | 3 | 7.04 | 4 | 6.21 | 4 | 5.09 | 5 | 5.03 | 3 |
| 74 | 25.30 | 74 | 12.54 | 34 | 8.32 | 10 | 7.10 | 6 | 6.27 | 6 | 5.72 | 4 | 5.12 | 7 | 4.58 | 18 |
| 76 | 40.79 | 100 | 20.31 | 12 | 13.61 | 14 | 10.23 | 18 | 6.80 | 14 | 4.65 | 21 | 4.44 | 33 | 4.26 | 41 |
| 77 | 28.46 | 100 | 9.60 | 1.0 | 7.18 | 10 | 4.75 | 4 | 4.61 | 1.3 | 4.44 | 0.8 | 4.23 | 2.5 | 4.00 | 6 |
| 78 | 40.63 | 75 | 20.32 | 35 | 13.53 | 14 | 10.15 | 21 | 6.78 | 15 | 5.00 | 43 | 4.69 | 100 | 4.49 | 4 |
| 79 | 12.11 | 22 | 11.93 | 14 | 9.91 | 14 | 8.48 | 38 | 6.06 | 31 | 5.45 | 47 | 5.41 | 31 | 5.28 | 25 |
| 80 | 21.15 | 42 | 10.51 | 12 | 4.67 | 13 | 4.35 | 11 | 4.28 | 8 | 4.07 | 100 | 3.83 | 10 | 3.63 | 12 |

| Example number | D | I | D | I | D | I | D | I | D | I | D | I | D | I | D | I |
|---|---|---|---|---|---|---|---|---|---|---|---|---|---|---|---|---|
| 61 | 3.78 | 22 | 3.69 | 44 | 3.56 | 30 | 3.419 | 11 | 3.300 | 10 | 3.237 | 8 | 3.158 | 8 | 3.120 | 7 |
| 62 | 3.80 | 100 | 3.69 | 21 | 3.55 | 25 | 3.50 | 27 | 3.308 | 47 | 3.168 | 30 | 3.017 | 41 | 2.247 | 30 |
| 63 | 3.91 | 26 | 3.82 | 21 | 3.490 | 6 | 3.394 | 6 | 3.360 | 7 | 3.190 | 100 | 3.138 | 9 | 2.962 | 10 |
| 64 | 3.89 | 20 | 3.54 | 100 | 3.408 | 95 | 3.278 | 14 | 3.108 | 12 | 2.887 | 22 | 2.781 | 17 | 2.622 | 12 |
| 65 | 4.25 | 27 | 3.76 | 31 | 3.72 | 100 | 3.65 | 8 | 3.326 | 9 | 3.320 | 11 | 3.294 | 8 | 3.095 | 7 |
| 66 | 3.65 | 26 | 3.496 | 16 | 3.406 | 7 | 3.352 | 5 | 3.228 | 10 | 3.081 | 6 | 2.951 | 5 | 2.092 | 12 |
| 67 | 3.78 | 30 | 3.71 | 8 | 3.63 | 22 | 3.53 | 15 | 3.432 | 11 | 3.402 | 12 | 3.335 | 10 | 3.123 | 9 |
| 68 | 3.73 | 13 | 3.58 | 15 | 3.487 | 25 | 3.404 | 2 | 3.314 | 7 | 3.202 | 2 | 3.123 | 10 | 2.903 | 2 |
| 69 | 4.04 | 78 | 3.88 | 59 | 3.83 | 32 | 3.60 | 37 | 3.50 | 31 | 3.436 | 23 | 3.307 | 14 | 3.271 | 15 |
| 70 | 4.28 | 4 | 4.10 | 12 | 4.03 | 5 | 3.96 | 8 | 3.91 | 5 | 3.67 | 4 | 3.59 | 5 | 3.53 | 5 |
| 71 | 3.91 | 66 | 3.77 | 27 | 3.66 | 49 | 3.52 | 22 | 3.397 | 24 | 3.247 | 14 | 3.169 | 9 | 3.111 | 11 |
| 72 | 4.26 | 7 | 4.09 | 13 | 3.95 | 14 | 3.87 | 6 | 3.69 | 5 | 3.63 | 6 | 3.57 | 6 | 3.51 | 3 |
| 73 | 4.55 | 30 | 3.96 | 3 | 3.82 | 100 | 3.421 | 34 | 3.401 | 51 | 3.155 | 6 | 2.241 | 3 | 1.961 | 3 |

TABLE VI-continued

| 74 | 3.98 | 3 | 3.86 | 100 | 3.420 | 25 | 3.211 | 4 | 3.167 | 5 | 3.041 | 5 | 2.846 | 3 | 2.042 | 5 |
|---|---|---|---|---|---|---|---|---|---|---|---|---|---|---|---|---|
| 76 | 4.20 | 38 | 3.95 | 63 | 3.67 | 41 | 3.54 | 17 | 3.415 | 11 | 3.276 | 10 | 3.139 | 8 | 3.114 | 8 |
| 77 | 3.79 | 4 | 3.64 | 1.3 | 3.59 | 1.0 | 3.53 | 5 | 3.408 | 2.2 | 3.338 | 1.0 | 3.136 | 1.3 | 2.823 | 1.1 |
| 78 | 4.37 | 65 | 4.02 | 23 | 3.74 | 12 | 3.66 | 8 | 3.494 | 17 | 3.352 | 8 | 2.238 | 5 | 2.074 | 4 |
| 79 | 4.51 | 22 | 4.29 | 21 | 4.21 | 20 | 3.71 | 100 | 3.63 | 19 | 3.443 | 17 | 3.309 | 25 | 3.091 | 22 |
| 80 | 3.58 | 18 | 3.471 | 17 | 3.375 | 7 | 3.264 | 38 | 3.160 | 13 | 2.937 | 8 | 2.166 | 12 | 2.104 | 8 |

Data in Tables I, III, and V clearly demonstrate a high qualitative correlation between SHG efficiency and moderate to strong pyroelectricity. The data also indicate a lower limit, below which the simple pyroelectric test used herein may be inaccurate. This limit may be reached in certain cases where the value of SHG efficiency is below one. Exact characterization of the crystal form must be effected by x-ray methods. Specifically, single-crystal x-ray analysis may be used to establish unambiguously both the chemical composition and crystal structure, including acentricity, of a material. For example, single-crystal x-ray structure analysis was done on the material of Example 60 and showed it to be centrosymmetric, in accordance with the pyroelectric and SHG results for this material. From data thus gathered, it is possible to compute with a high degree of accuracy the x-ray powder pattern of a "perfect" (i.e., randomly oriented) powder of that same crystal form. The results are shown in Table IV, Example 60A. This pattern can then be compared with the experimental x-ray powder pattern of the sample, to prove identity or non-identity. Such a comparison may be made between Examples 60 and 60A in Table IV.

Data in Tables I and II show the dramatic effects of the crystallizing technique and/or crystallization solvent on SHG efficiency. For example, the $C_7$ urethanes crystallized from n-butyl acetate, ether, and especially ethanol, i.e., Examples 7 and 26–29, all showed different SHG Values. Their powder x-ray patterns differed markedly. From these results, one can conclude that orientation of the SHG active portion of the molecule is sensitive to solvents. The solvent can act either to enhance the desired parallel arrangement of the SHG active moiety or perhaps favor an unwanted antiparallel alignment; however, it is not the sole influence upon the alignment.

For a given solvent, the crystallizing temperature can also affect SHG efficiency of the solid product. For example, when the $C_5$ urethane was crystallized from aqueous ethanol, two crops of crystals were obtained, i.e., Examples 5 and 39. Their powder x-ray patterns, while similar, are distinguished by relatively strong lines at 3.356Å and 3.425Å, among others. The first crop of crystals was harvested as the hot mixed solvent was cooling to a warm temperature (above room temperature) while the other crop of crystals was harvested when the warm solvent had cooled to room temperature. The first crop of crystals had a SHG efficiency of 46, while the second crop had a SHG efficiency of 0.03. This factor of greater than 1000 in SHG efficiency leads one to suspect that the second crop of crystals were actually inactive but contaminated by a small amount of the first, which would account for the small SHG value and the pyroelectric results.

When the $C_2$ urethane was crystallized from hot ethanol, two crops of crystals, i.e., Examples 2 and 44, were obtained. The first crop of crystals, which were fine needles, showed a SHG efficiency of 23.4, while the second crop of crystals, which were chunky and diamond-shaped, showed a SHG efficiency of 5.5. While crystal forms may sometimes be an indication of real differences in crystal structures, it is well known even for common table salt that the same internal structure of a material, as shown by x-ray powder patterns, can yield quite differently-shaped crystals when one or another facet's growth is retarded by solvents or impurities. In the case of Examples 2 and 44, the d-values for the powder x-ray lines, and their relative intensities, are in sufficiently close agreement as to be judged identical in crystal structure. It is in no way surprising that the SHG efficiencies differ by a factor of about four, since it is impossible to crush crystal forms so dissimilar in aspect ratio to identical coarse powders. Differences in average dimension or in aspect ratio can be expected to affect SHG efficiency measurements by perhaps as much as a factor of ten.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A second harmonic generator comprising a laser source of coherent light radiation at a fixed fundamental frequency, an acentrically crystalline, achiral, organic compound, means for directing the output radiation of the laser onto said compound, and output means for utilizing the second harmonic frequency, said compound being a straight-chain N-nitrophenyl carbamyl compound crystallized in a non-centrosymmetric configuration, said crystalline compound being transparent to radiation at said fixed fundamental frequency and said second harmonic frequency, and said crystalline compound being a derivative of an N-nitrophenyl carbamic acid such that the straight chain is linked to the carbamyl carbon atom by an oxygen atom or nitrogen atom.

2. The second harmonic generator of claim 1, wherein said compound is selected from a group represented by the formulae:

$$R^1HNCONHR^2 \quad (I)$$

and $$R^1HNCO_2R^2 \quad (II)$$

where $R^1$ represents one member of a group consisting of a nitrophenyl and substituted nitrophenyl group, and $R^2$ represents a group having two to twenty-two catenated methylene groups terminated by $R^3$, where $R^3$ represents a member selected from the group consisting of hydrogen, halogen, unsubstituted ethinyl group, substituted ethinyl group, unsubstituted vinyl group, substituted vinyl group, hydroxy group, alkoxy group, aryloxy group, acyloxy group, alkanesulfonyloxy group, arenesulfonyloxy group, alkanesulfonyl group, arenesulfonyl group, aryloxysulfonyl group, alkylthio group, arylthio group, cyano group, unsubstituted carbonyl, substituted carbonyl group, unsubstituted aryl group, substituted aryl group, unsubstituted amino group, substituted amino group, acyl amino group, and heterocyclic group.

3. The second harmonic generator of claim 1, wherein said compound is selected from a group represented by the formulae:

$$R^1HNCONHR^2 \qquad (I)$$

and $$R^1HNCO_2R^2 \qquad (II)$$

where $R^1$ represents one member of a group consisting of an unsubstituted nitrophenyl group and a substituted nitrophenyl group, and $R^2$ represents a polymethylene group having two to twenty-two catenated methylene groups terminated by one member of a group consisting of a hydrogen atom, a halogen atom, an unsubstituted vinyl group, a substituted vinyl group, an unsubstituted ethinyl group, a substituted ethinyl group, an unsubstituted aryl group, a substituted aryl group, a hydroxy group, an ether group, an ester group, a thioether group, and a thiolester group.

4. The second harmonic generator of claim 1, wherein said laser is a Nd-YAG laser.

5. The second harmonic generator of claim 1, wherein said laser is a solid-state laser.

6. A process for converting a fixed fundamental frequency of coherent laser light into a second harmonic frequency which comprises passing said laser light through a nonlinear optical element comprising an acentrically crystalline, achiral, organic compound, said compound being a straight-chain N-nitrophenyl carbamyl compound crystallized in a non-centrosymmetric configuration, said crystalline compound being transparent to said fixed fundamental frequency and to said second harmonic frequency, and said crystalline compound being a derivative of an N-nitrophenyl carbamic acid such that the straight chain is linked to the carbamyl carbon atom by one member of a group consisting of an oxygen atom and nitrogen atom.

7. The process of claim 6, wherein said acentrically crystalline compound is selected from a group represented by the formulae:

$$R^1HNCONHR^2 \qquad (I)$$

and $$R^1HNCO_2R^2 \qquad (II)$$

where $R^1$ represents one member of a group consisting of a nitrophenyl and substituted nitrophenyl group, and $R^2$ represents a group having two to twenty-two catenated methylene groups terminated by $R^3$, where $R^3$ represents a member selected from the group consisting of hydrogen, halogen, unsubstituted ethinyl group, substituted ethinyl group, unsubstituted vinyl group, substituted vinyl group, hydroxy group, alkoxy group, aryloxy group, acyloxy group, alkanesulfonyloxy group, arenesulfonyloxy group, alkanesulfonyl group, arenesulfonyl group, aryloxysulfonyl group, alkylthio group, arylthio group, cyano group, unsubstituted carbonyl, substituted carbonyl group, unsubstituted aryl group, substituted aryl group, unsubstituted amino group, substituted amino group, acyl amino group, and heterocyclic group.

8. The process of claim 6, wherein said acentrically crystalline compound is selected from a group of represented by the formulae:

$$R^1HNCONHR^2 \qquad (I)$$

and $$R^1HNCO_2R^2 \qquad (II)$$

where $R^1$ represents one member of a group consisting of an unsubstituted nitrophenyl group and a substituted nitrophenyl group, and $R^2$ represents a polymethylene group having two to twenty-two catenated carbon atoms terminated by a hydrogen atom, a halogen atom, an unsubstituted vinyl group, a substituted vinyl group, an unsubstituted ethinyl group, a substituted ethinyl group, an unsubstituted aryl group, a substituted aryl group, a hydroxy group, an ether group, an ester group, a thioether group, and a thiolester group.

* * * * *

UNITED STATES PATENT AND TRADEMARK OFFICE
CERTIFICATE OF CORRECTION

PATENT NO. : 5,059,002

DATED : October 22, 1991

INVENTOR(S) : Francis et al.

It is certified that error appears in the above-indentified patent and that said Letters Patent is hereby corrected as shown below:

Col. 5, line 1, "pulses Urea" should be --pulses. Urea--.

Col. 7, line 5, "point see" should be --point; see--.

Signed and Sealed this

Seventeenth Day of May, 1994

Attest:

BRUCE LEHMAN

*Attesting Officer*   *Commissioner of Patents and Trademarks*